(12) United States Patent
Suhadolnik et al.

(10) Patent No.: US 6,281,201 B1
(45) Date of Patent: Aug. 28, 2001

(54) BASE-MODIFIED DERIVATIVES OF 2',5'-OLIGOADENYLATE AND ANTIVIRAL USES THEREOF

(75) Inventors: Robert J. Suhadolnik, Roslyn, PA (US); Wolfgang Pfleiderer, Constance (DE)

(73) Assignee: Temple University- of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/445,552

(22) PCT Filed: Jun. 1, 1998

(86) PCT No.: PCT/US98/11095

§ 371 Date: Dec. 8, 1999

§ 102(e) Date: Dec. 8, 1999

(87) PCT Pub. No.: WO98/56385

PCT Pub. Date: Dec. 17, 1998

Related U.S. Application Data

(60) Provisional application No. 60/052,027, filed on Jul. 9, 1997, and provisional application No. 60/049,404, filed on Jun. 12, 1997.

(51) Int. Cl.$^7$ .............................. A61K 31/70; A01G 7/06
(52) U.S. Cl. ................................ 514/44; 514/81; 514/93; 536/25.2; 536/25.6; 536/26.22; 536/26.26; 544/244; 548/266.8
(58) Field of Search .................... 544/244; 548/266.8; 514/81, 93, 44; 536/25.6, 26.2, 26.26, 25.2

(56) References Cited

U.S. PATENT DOCUMENTS

| | | | |
|---|---|---|---|
| 4,464,359 | 8/1984 | Suhadolnik et al. | 424/180 |
| 4,859,768 | 8/1989 | Suhadolnik et al. | 536/27 |
| 4,924,624 | 5/1990 | Suhadolnik et al. | 47/58 |
| 4,981,957 | 1/1991 | Lebleu et al. | 536/27 |

FOREIGN PATENT DOCUMENTS

| | | |
|---|---|---|
| 2 002 773 | 2/1979 | (GB) . |
| WO 89/12380 | 12/1989 | (WO) . |
| WO 93/17692 | 9/1993 | (WO) . |
| WO 96/08256 | 3/1996 | (WO) . |

OTHER PUBLICATIONS

Kvasyuk, E.I. et al., Synthesis and Biological Activity of New 2',5'–Oligonucleotides, *Nucleosides & Nucleotides*, 16(7–9):1351–1354 (Nov. 1997).

Kvasyuk, E.I. et al., "Synthesis and Biological Activity of New Base–Modified (2',5') Oligoadenylate Trimers", *Helvetica Chimica Acta*, 80(4):1053–1060 (Jun. 30, 1997).

Beaucage and Iyer, "The Functionalization of Oligonucleotides Via Phosphoramidite Derivatives", *Tetrahedron*, 49(10):1925–1993 (1993).

*Primary Examiner*—Richard L. Raymond

(74) *Attorney, Agent, or Firm*—Drinker Biddle & Renth LLP

(57) ABSTRACT

Antiviral compounds have the formula

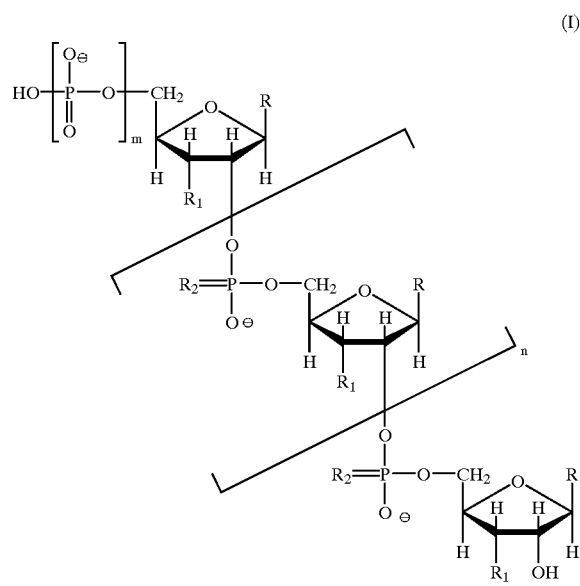

(I)

wherein m is zero, 1, 2 or 3; n is from 1 to 8, preferably 1, 2 or 3; most preferably 1 or 2;

R is independently selected from the group consisting of

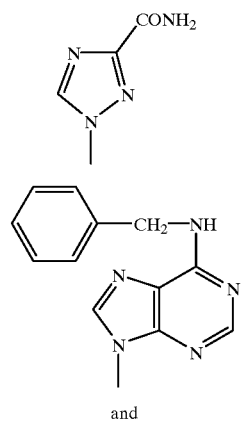

and

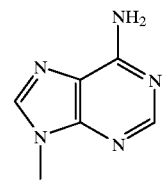

provided that all R may not be
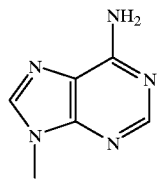
$R_1$ is independently selected from the group consisting of hydroxyl and hydrogen;
$R_2$ is independently selected from the group consisting of oxygen and sulfur;
or water soluble salts thereof.
20 Claims, No Drawings

BASE-MODIFIED DERIVATIVES OF 2',5'-OLIGOADENYLATE AND ANTIVIRAL USES THEREOF

CROSS-REFERENCE TO RELATED APPLICATIONS

This application is the U.S. National Phase of PCT/US98/11095 pursuant to 35 U.S.C. 371, which claims the benefit of U.S. provisional application Ser. No. 60/049.404, filed Jun. 12. 1997 and U.S. provisional application Ser. No. 60/052.027, filed Jul. 9. 1997.

FIELD OF THE INVENTION

This invention relates to synthetic analogues of naturally occurring antiviral 2',5'-oligoadenylates wherein at least one of the nucleoside residues is replaced with a modified nucleoside.

BACKGROUND OF THE INVENTION

The discovery of the 2'-5' oligoadenylates is connected with the study of the mechanisms of interferon action as the cellular response to virus infection [2]. The 5'-triphosphate of the (2'-5') oligoadenylate trimer plays a most important role in the antiviral mechanism induced by interferon [3]. It is generally regarded that activation of RNase L by 2-5A is key to the antiviral defense mechanisms. Interferon induces transcription of the enzyme 2-5A synthetase which produces 2',5'-linked oligoadenylates upon activation of double-stranded RNA.

Previously, the only known biochemical effect of 2-5A is activation of RNase L. This enzyme hydrolyzes mRNA and rRNA, thereby resulting in inhibition of protein synthesis. The activation of RNase L is transient unless 2-5A is continuously synthesized, since 2-5A is rapidly degraded. RNase L activation thus plays a critical role in inhibiting replication, and therefore in defending against infection by viruses.

Naturally occurring (2'-5')oligoadenylates (both 5'-phosphorylated and unphosphorylated) have shown different kinds of biological activity [4][5]. Analogues of the natural (2'-5')oligoadenylates have been synthesized to achieve new approaches to antiviral and antitumoral therapy [6-13]. Biological activities of 5'-phosphorylated (2'-5') oligoadenylates are connected with the functioning of the (2'-5')A system which leads to the inhibition of protein synthesis [3]. The mechanism of action of unphosphorylated (2'-5')oligoadenylates in many cases is still unknown. Recently, certain sugar-modified trimers of (2'-5') oligoadenylates were found to be inhibitors of HIV-1 reverse transcriptase (RT) [14-18].

SUMMARY OF THE INVENTION

The compounds of the present invention are useful in inhibiting viral infections in plants and mammals.

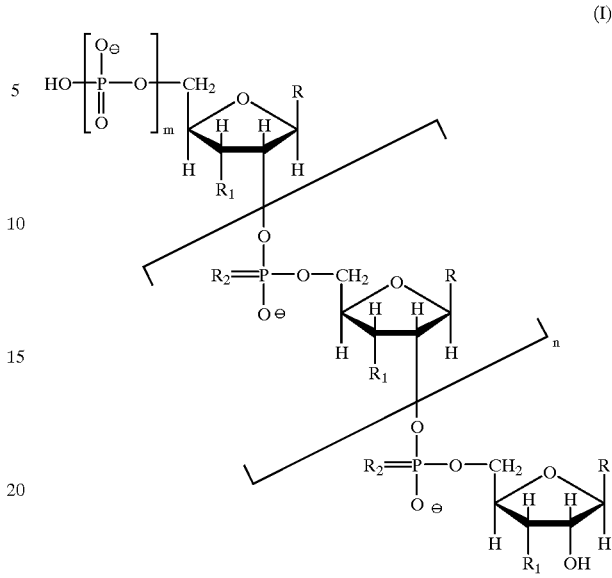

(I)

The compounds and the water-soluble salts thereof are of the formula wherein m is zero, 1, 2 or 3; n is from 1 to 8, preferably 1, 2 or 3; most preferably 1 or 2;

R is independently selected from the group consisting of

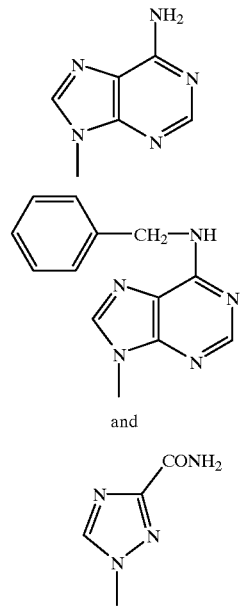

and provided that all R may not be

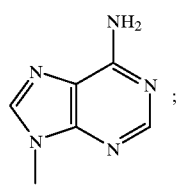

$R_1$ is independently selected from the group consisting of hydroxyl and hydrogen;

$R_2$ is independently selected from the group consisting of oxygen and sulfur.

Preferably, all $R_1$ are hydroxyl and all $R_2$ are oxygen.

According to one preferred embodiment of the invention, R is selected from the group consisting of

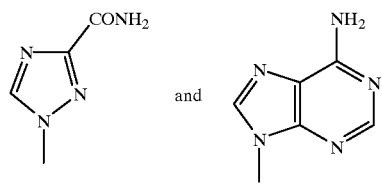

and

According to another preferred embodiment of the invention, R is selected from the group consisting of

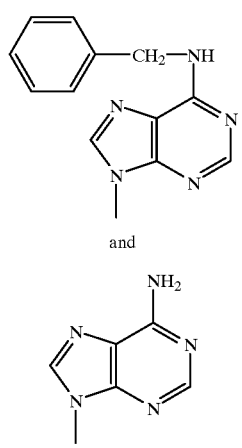

and

According to yet another preferred embodiment of the invention, the R of the 2',3'-terminal nucleoside moiety is

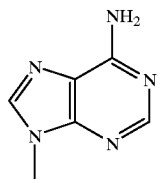

Compounds of the invention include, for example, the following core compounds, the 5'-mono, di-, and triphosphates thereof, and water-soluble salts of any of them:

adenylyl-(2'-5')-adenylyl-(2'-5')-1-(β-D-ribofuranosyl)-1H-1,2,4-triazole-3-carboxamide;

adenylyl-(2'-5')-[1-(β-D-ribofuranosyl)-1H-1,2,4-triazole-3-carboxamide]yl-(2'-5')-adenosine;

1-(β-D-ribofuranosyl)-1H-1,2,4-triazole-3-carboxamide]yl-(2'-5')-adenylyl-(2'-5')-adenosine;

adenylyl-(2'-5')-adenylyl-(2'-5')-$N^6$-benzyladenosine;

adenylyl-(2'-5')-$N^6$-benzyladenylyl-(2'-5')-adenosine;

$N^6$-benzyladenylyl-(2'-5')-adenylyl-(2'-5')-adenosine; and $N^6$-benzyladenylyl-(2'-5')-$N^6$benzyladenylyl-(2'-5')-$N^6$-benzyladenosine.

The invention also comprises a method of treating viral infection in mammals or plants by administering an antivirally effective amount of a compound according to the above formula, or a water-soluble salt thereof. The invention further comprises an antiviral composition comprising such a compound or water soluble salt in combination with an agricultural carrier or pharmaceutical carrier.

DETAILED DESCRIPTION OF THE INVENTION

Replacement of the adenine moiety in the (2'-5') oligoadenylate trimer core with 1H-1,2,4-triazole-3-carboxamide (TCA) or with $N^6$-(benzylamino)purine ($Ade^{Bn}$)-moieties has resulted in a new group of inhibitors of HIV-1 replication. Trimer compounds of the present invention and their synthesis intermediates are numbered 1 through 28 as follows for purposes of identification. Compound 29 is the authentic (2'-5')oligoadenylate trimer core.

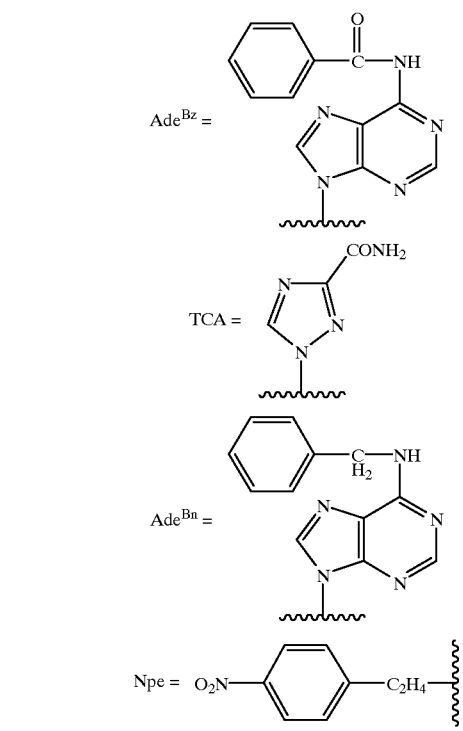

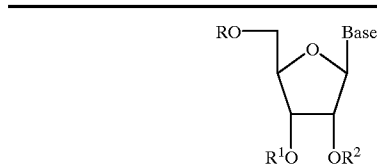

| | Base | R | $R^1$ | $R^2$ |
|---|---|---|---|---|
| 1 | $Ade^{Bn}$ | H | H | H |
| 2 | $Ade^{Bn}$ | MeOTr | H | H |
| 3 | $Ade^{Bn}$ | MeOTr | Bz | Bz |
| 4 | $Ade^{Bn}$ | MeOTr | H | Bz |
| 5 | $Ade^{Bn}$ | MeOTr | Bz | H |
| 6 | $Ade^{Bn}$ | H | Bz | Bz |
| 7 | TCA | H | H | H |
| 8 | TCA | MeOTr | H | H |
| 9 | TCA | MeOTr | Bz | Bz |
| 10 | TCA | MeOTr | Bz | H |
| 11 | TCA | H | Bz | Bz |
| 12 | $Ade^{Bz}$ | H | Bz | Bz |

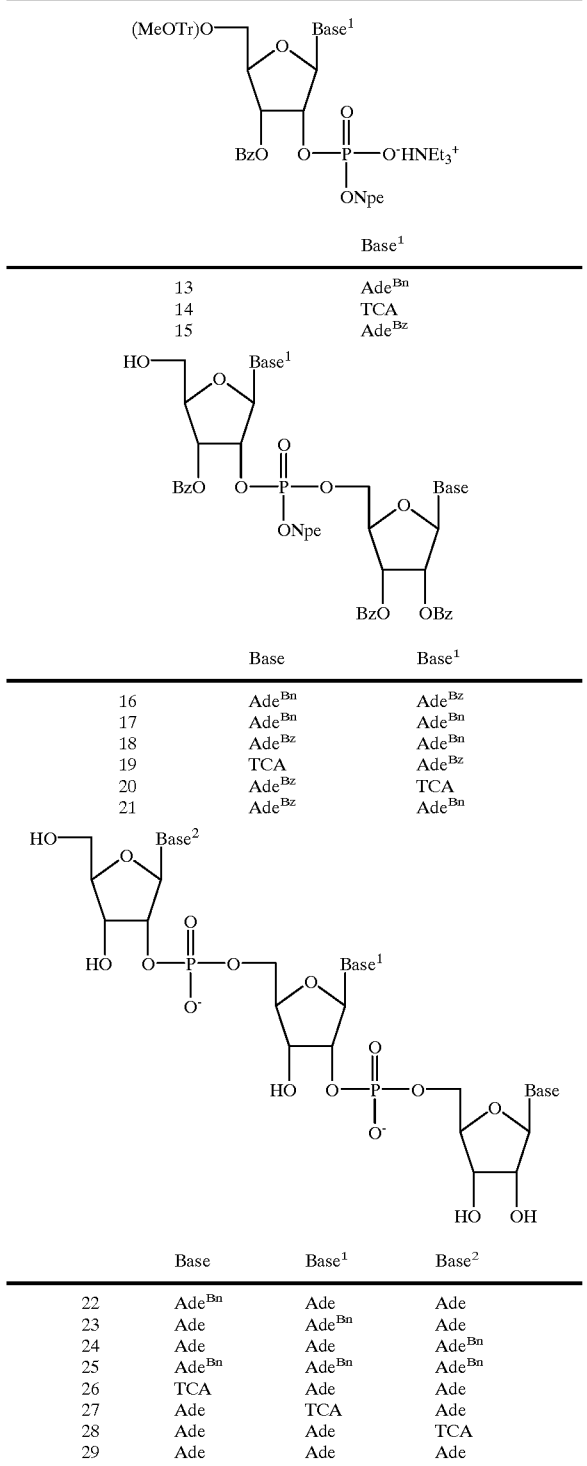

| | Base | Base¹ |
|---|---|---|
| 16 | Ade^Bn | Ade^Bz |
| 17 | Ade^Bn | Ade^Bn |
| 18 | Ade^Bz | Ade^Bn |
| 19 | TCA | Ade^Bz |
| 20 | Ade^Bz | TCA |
| 21 | Ade^Bz | Ade^Bn |

| | Base | Base¹ | Base² |
|---|---|---|---|
| 22 | Ade^Bn | Ade | Ade |
| 23 | Ade | Ade^Bn | Ade |
| 24 | Ade | Ade | Ade^Bn |
| 25 | Ade^Bn | Ade^Bn | Ade^Bn |
| 26 | TCA | Ade | Ade |
| 27 | Ade | TCA | Ade |
| 28 | Ade | Ade | TCA |
| 29 | Ade | Ade | Ade |

In the compounds of the present invention, each $R_2$ may be oxygen, each $R_2$ may be sulfur, or $R_2$ may comprise a mixture of oxygen and sulfur to provide a backbone of a 2',5'-phosphodiester, a 2',5'-phosphorothioate or a 2',5'-mixed phosphorothioate/phosphodiester oligonucleotide, respectively.

The substitution of sulfur for oxygen in the 2',5'-phosphodiester backbone referenced above, introduces chirality into the molecules and introduces a new chemistry of the backbone. The core 2',5'-phosphorothioates exhibit increased resistance to phosphodiesterase and phosphatases and new biological activities compared to authentic 2-5A cores. The preparation of the 2',5'-phosphorothioates, including fully resolved enantiomers thereof, is disclosed in U.S. Pat. No. 4,924,624 and is incorporated herein by reference. A mixture of phosphorothioate and phosphodiester linkages is possible in the same oligomer, providing molecules with a mixed phosphodiester/phosphorothioate backbone, as described in PCT/US95/10683, the entire disclosure of which is incorporated by reference.

While the preparation and examples that follow are directed to oligomers of a base-modified adenosine, the procedure described is equally applicable to the manufacture of oligomers comprising a base-modified cordycepin, or mixed chain of cordycepin and adenosine residues as described in U.S. Pat. No. 4,859,768, the entire disclosure of which is incorporated by reference.

Chemical Synthesis

Syntheses of the compounds of the present invention may be achieved by the phosphotriester method using a published approach [19]. Synthetic $N^6$-benzyladenosine 1 and 1-(β-D-ribofuranosyl)-1H-1,2,4-triazole-3-carboxamide 7, obtained by the reaction of microbiological transglycosylation as described before [20], are converted into the corresponding selectively blocked nucleosides 2-6 and 8-11 and corresponding nucleotides 13 and 14, respectively. Thus, treatment of 1 with monomethoxytrityl chloride (MeOTrCl) in pyridine gives the 5'-O-monomethoxytrityl derivative 2 (85%). Benzoylation of 2 with benzoyl cyanide (BzCN) in MeCN [19] leads to a mixture of the 2',3'-di-O-benzyl 3, 2'-O-benzoyl 4, and 3'-O-benzoyl 5 derivatives which are isolated by column chromatography (CC) in 38, 13, and 46% yield, respectively. Treatment of 3 with a 2% solution of TsOH in $CH_2CL_2$/MeOh 7:3 affords 2',3'-di-O-benzoyl-$N^6$-benzyladenosine 6 in 96% yield. Similarly, 7 is converted into the 5'-O-monomethoxytrityl derivatives 8–10 in 92, 16, and 57% yield, respectively. Detritylation of 9 leads to the 5'-OH derivative 11 in 78% yield. Furthermore, the reaction of the 3'-O-benzoylated compounds 5 and 10 with 2-chlorophenyl bis (1H-1,2,4-triazol-1-yl)-phosphinate followed by subsequent treatments with 2-(4-nitrophenyl)-ethanol (NpeOH) and then a solution of 4-nitrobenzaldoxin in dioxane/$H_2O$/$Et_3N$ 1:1:1, gives the corresponding nucleoside 2'-phosphodiesters 13 and 14 which are isolated by CC (silica gel) in 82 and 48% yield, respectively.

The compounds 6, 11, 13, and 14 and the corresponding adenosine derivatives 12 [21] and 15 [22] are then used in the syntheses of the new. (2'-5')oligonucleotide trimers 22–29. Condensation of 2',3'-di-O-benzoyl-$N^6$-benzyladenosine 6 with the 2'-phosphodiester 15 in pyridine in the presence of a mixture of 1H-triazole/2,4,6-triisopropylbenzenesulfonyl chloride (TpsCl) 3:1, followed by detritylation, leads to the 5'-OH dimer 16 which is isolated by CC in 85% yield. Similar reaction sequences convert compounds 6 and 13, 12 and 13, 11 and 15, and 12 and 14, into the corresponding 5'-OH dimers 17–20, isolated in 81, 87, 74, and 76% yield, respectively. The synthesis of 5'-OH dimer 21 has been described earlier [22].

The transformations of the dimers 16–20 to the trimer level is afforded the same techniques consisting of a condensation step and followed by successive treatment with 2% solution of TsOH, 0.5M DBU (1,8diazabicyclo[5.4.0] undec-7-ene)/(pyridine, and $NH_3$/MeOH, respectively, to remove the three different protecting groups. Final purification by CC(DEAE-cellulose)ion exchange gives the trimers 22–28 in good to moderate yields.

Biological Utility

The compounds of the present invention may be combined with appropriate pharmaceutical or agricultural carriers to form an antiviral composition.

For pharmaceutical use, the compounds of the invention may be taken up in pharmaceutically acceptable carriers, such as, solutions, suspensions, tablets, capsules, ointments, elixirs and injectable composition and the like. They are administered to subjects suffering from viral infection. The dosage administered depends upon the nature and severity of the infection, the disease stage, and, when administered systematically, the size and weight of the infected subject.

The compounds are generally administered in the form of water-soluble salts. Pharmaceutically acceptable water soluble salts include, for example, the sodium, potassium or ammonium salts of the active compounds. They are readily dissolved in water or saline solution. Thus, the preferred formulation for pharmacological use comprises a saline solution of the desired compound in salt form. The formulation may further contain an agent, such as a sugar or protein, to maintain osmotic balance. The salt form of the compound is preferred owing to the relatively high acidity (about pH 3) of the acid form of the compounds.

The compounds of the invention may be used as a treatment for humans and animals from viral infectives such as Herpes simplex, rhinovirus, hepatitis and other infections of the hepatitis virus family, Epstein Barr virus, measles virus, multiple sclerosis (which may be caused by a viral agent) and the various Human Immunodeficiency Viruses ("HIV"), such as HIV-1, which causes cutaneous T cell lymphoma, HIV-2, which causes Sezary lymphoma, and HIV-3, which is responsible for Acquired Immune Deficiency Syndrome ("AIDS"). The compounds of the invention inhibit HIV-1 induced syncytia formation.

The compounds may be applied topically to treat skin cancers caused by radiation, carcinogens or viral agents. Such skin cancers include cutaneous T-cell lymphoma, Sezary lymphoma, Xeroderma pigmentosium, ataxia telangiectasia and Bloom's syndrome. A sufficient amount of a preparation containing a compound of the invention is applied to cover the lesion or affected area. An effective concentration of active agent is between about $10^{-3}$ M and $10^{-5}$ M, with $10^{-4}$ M being preferred.

The compounds of the present invention may also be used to treat plant-infecting viruses, particularly tobacco mosaic virus, and other viruses which cause necrosis in turnips, cucumbers, orchids and in other plants. Such viruses include, but are not limited to, tobacco vein mottling virus, vesicular stomatitis virus, vaccinia virus, turnip necrosis virus, and cymbidium orchid virus.

The compounds may be administered effectively to plants by topical application by abrasion of the leaf surface, aerosol spray, treatment of the soil, spraying, or dusting.

An effective antiviral composition may be formed by combining one or more of the compounds of the invention with a carrier material suitable for agricultural use. The active compound may also be administered by spraying insect vectors such as aphids, thrips and whiteflies which carry virus to plants. The dosage administered depends upon the severity of the infection.

The compounds of the invention may be applied to plant seeds prior to germination to control viruses contained in the germ plasm. The seeds may be soaked in a solution of polyethylene glycol ("PEG") containing one or more of the compounds. PEG brings the seeds to physiological activity and arrest. The relative concentration of active compound to PEG depends upon the type of seed under treatment.

Plants may be effectively treated with an aqueous formulation containing from about $10^{-1}$ to about $10^{-2}$ M concentration of active ingredient. The compounds of the invention may be applied at very low concentrations. An effective amount of active ingredient on the plant surface is from about $10^{-8}$ to about $10^{-12}$ mole per cm$^2$ of plant surface area, with about $10^{-10}$ mole to about $10^{-12}$ mole per cm$^2$ being preferred. For the typical tobacco plant, $10^{-5}$ M of compound is effective. At this rate, one pound of active ingredient is sufficient to treat $2 \times 10^8$ tobacco plants.

For agricultural application, the compounds are advantageously administered in the form of water-soluble salts, e.g. ammonium or potassium salts. Sodium salts are generally avoided in treating edible plants.

The compounds of the invention are readily dissolved in water, particularly at such low concentrations. Aqueous formulations for agricultural use may optionally contain a sticker and/or a UV-stabilizer. Such agents are well-known to those skilled in the art. Fatty acids (1%) are useful as spreader sticker agents. Effective UV-stabilizers include, for example, p-aminobenzoic acid.

For antiviral use in mammals, the compounds of the invention are administered parenterally, such as intravenously, intraarterially, intramuscularly, subcutaneously or when administered as an anti-cancer agent, intratumorally. The preferred route of administration for antiviral therapy is intravenous injection. The compounds of the invention may be administered to mammals at very low concentrations. The actual dosage administered may take into account the size and weight of the patient, whether the nature of the treatment is prophylactic or therapeutic in nature, the age, health and sex of the patient, the route of administration, the nature and stage of the affliction, and other factors. An effective daily dosage of active ingredient, based upon in vivo studies involving other 2-5A analogues, is from about 0.25 g per 70 kg of body weight (approximately 152 lbs) to about 2.5 g per 70 kg of body weight. The preferred daily dosage is about 0.5 g per 70 kg of body weight. Those skilled in the art should readily be able to derive appropriate dosages and schedules of administration to suit the specific circumstance and needs of the patient.

It is expected that an effective treatment regimen includes administration of the daily dosage for two days. Treatment is continued at least until the disease condition is substantially abated.

Preferably, the therapeutic end point is determined by testing for the continued presence of viral DNA. Such testing can be done by polymerase chain reaction (PCR) in which the presence of viral DNA is assayed according to conventional PCR. PCR primers of appropriate nucleotide sequences for amplification of viral DNA can be prepared from known viral nucleotide sequences. To obtain DNA for testing, patient peripheral blood mononuclear cells are lysed with an appropriate lysing agent, such as NP-40.

Alternatively, testing for the continued presence of the virus can be performed by an antigen-antibody assay using any of the known monoclonal or polyclonal antisera against a protein antigen of the target virus protein coat. For example, an antigen-antibody assay may be employed to detect any of the protein antigen in the virus HIV protein coat, for example, the gp120, p17 or p24. Moreover, the target antigen is not limited merely to coat protein antigens. Antisera can be targeted against a suitable non-coat protein antigen, such as the HIV reverse transcriptase (RT) molecule. Monoclonal antibodies to HIV RT are known. Sobol et al., *Biochemistry* 1991, 30, 10623.

Additionally, testing for the presence of the infecting virus during or post-treatment could be accomplished by an assay which assesses the viral load in the patient's blood stream. This can be done by determining syncytia formation. See procedure outlined in Henderson et al., *Virology,* 1991, 182, 186.

In addition to administration with conventional carriers, the compounds of the present invention may be administered by a variety of specialized oligonucleotide or nucleic acid delivery techniques. 2-5A and its analogues have been successfully encapsulated in various encapsulating materials, such as in unilamellar liposomes and delivered with the aid of monoclonal antibodies to cells, Bayard et al., *Eur. J. Biochem.,* 1985, 151, 319. Reconstituted Sendai virus envelopes have been successfully used to deliver RNA and DNA to cells, Arad et al., *Biochem. Biophys. Acta.* 1986, 859, 88. Moreover, the virus envelope is not limited to Sendai virus, but could include encapsulation in any retroviral amphotrophic particle. For example, an HIV envelope could be formed from any part or all of the outer protein coat of a non-infectious HIV particle. Such particles as gp 120 can be cloned by known recombinant techniques. These techniques may be utilized for introduction of the present 2-5A oligoadenylate derivatives into cells. It is further contemplated that the compounds of the invention may be administered in the form of prodrugs in which lipophilic groups are attached to, for example, the 5'-terminal hydroxyl group of the core compound.

Biological Studies

Three studies were performed to determine the antiviral activity of the (2'-5')oligonucleotide derivatives of the present invention: (i) inhibition of HIV-1-replication, (ii) inhibition of HIV-1 reverse-transcriptase (RT) activity, and (iii) activation of recombinant human GST-RNase L. All compounds were tested at a concentration of 300 $\mu$M.

Inhibition of HIV-1 Replication

The infected centers assay as described by Henderson et al., *Virology* 1991, 182, 186, was used to measure the ability of the trimer core compounds of the invention to inhibit HIV-1 induced syncytia formation, an indicator of HIV-1 replication in T cells. Freshly isolated peripheral blood lymphocytes (PBL) were treated with 2-5A trimer or derivatives for 2 hours and infected with HIV-1 strain IIIB at a multiplicity of infection of approximately 0.1. The infected PBL were maintained in RPMI-1640 medium supplemented with 10% (v/v) heat-inactivated fetal calf serum at 37° C. in a humidified 5% $CO_2$ in air atmosphere. After 48 hours, the cells were washed twice in Hank's balanced salt solution, serially diluted and seeded into multiple wells of a 96-well microtiter plate. Immediately, $2 \times 10^5$ exponentially growing Sup T1 cells were added to each well; Sup T1 cells readily form a syncytium with a cell which is productively infected with HIV-1. The wells were examined daily for the presence of syncytia, using a tissue culture microscope. The first signs of syncytia formation can be seen in 12 hours, with some complete syncytia developing by 24 hours. Final results were read at 72 hours. Each syncytium was counted as a single infected cell. The number of syncytia per seeded cell is determined and expressed as an infected center per infected cell. The number of syncytia per $10^4$ cells was 121±16 for the control Sup T1 cells. The data is shown in Table 1. The mean of triplicate determinations is shown; variance did not exceed 5–10%.

Inhibition of HIV-1 Reverse-Transcriptase Activity

Sup T1 cells were treated with trimer core compound at 300 $\mu$M for 6 hours and then infected with HIV-1 at a multiplicity of infection of approximately 0.1. At 96 hours post-infection, culture supernatant was removed and HIV-1 RT activity was assayed in triplicate as described by Henderson et al., *Virology* 1991, 182, 186. Briefly in this method, 25 $\mu$l of culture supernatant was added to a 50 $\mu$l cocktail containing 50 mM Tris (pH 8.0), 20 mM dithiothreitol, 10 mM $MgCl_2$, 60 mM NaCl, 0.05% Nonidet p-40, 5 $\mu$g/ml oligodeoxythymidylic acid, 10 $\mu$g/ml polyriboadenylic acid, 10 $\mu$M deoxythymidine triphosphate and 1mCi [$\alpha^{32}P$] thymidine 5'-triphosphate. The mixture was incubated at 37° C. for 2 hours. Fifty microliters of the cocktail were then spotted onto diethylaminoethyl (DEAE) paper, dried, washed with 2xSSC solution (three times for 10 minutes each time) and 95% ethanol (two times for 5 minutes each time), dried and exposed to radiographic film for 18 to 24 hours at −80° C. The filters were cut and final quantitation was determined by scintillation spectrometry.

The data for the HIV-1 RT activity is shown in Table 1 as a percent of RT activity. Control values for RT activity ranged from 15,000 to 16,000 dpm [$\alpha^{32}P$] incorporated. The mean of duplicate determinations is shown in Table 1. Variance did not exceed 5–10%.

Activation of Recombinant Human GST-RNase L

Human recombinant RNase L was expressed in *E. coli* (DH5$\alpha$) as a fusion protein of glutathione-S-transferase (GST). Activation of human recombinant GST-RNase L was measured as the percent of poly(U)[$^{32}P$]pCp hydrolyzed in the presence of authentic 2',5'-oligoadenylate trimer core or trimer core analog of the invention as described by Sobol et al., *J. Biol. Chem.* 1995, 270, 5963. The data is shown in Table 1 as the mean of duplicate determinations. Variance did not exceed 5–10%.

Results of Biological Studies

TABLE 1

Inhibition of HIV-1-Replication and Biological Activities of (2'–5') Oligonucleotide Trimers 22–29[a]

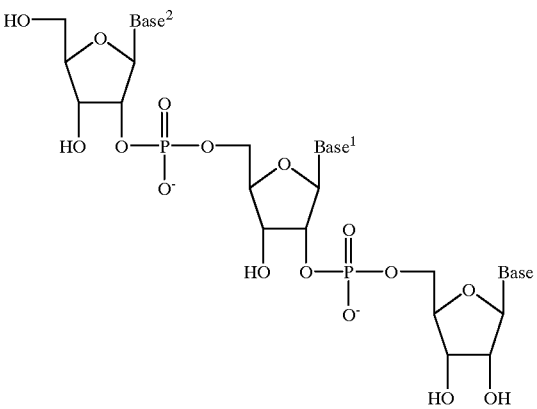

| | Base | Base[1] | Base[2] | Syn[b] | RT[c] | RNase L[d] |
|---|---|---|---|---|---|---|
| 22 | Ade[Bn] | Ade | Ade | >1500 | 33 | 37.4 |
| 23 | Ade | Ade[Bn] | Ade | >1500 | 7.6 | 34.8 |
| 24 | Ade | Ade | Ade[Bn] | >1500 | 16.7 | 0 |

TABLE 1-continued

Inhibition of HIV-1-Replication and Biological Activities of (2'–5') Oligonucleotide Trimers 22–29[a]

| Base | Base[1] | Base[2] | Syn[b] | RT[c] | RNase L[d] |
|------|---------|---------|--------|-------|------------|
| 25 | Ade[Bn] | Ade[Bn] | Ade[Bn] | >1500 | 10.6 | 13.6 |
| 26 | TCA | Ade | Ade | 1.6 | 99.7 | 87.7 |
| 27 | Ade | TCA | Ade | 7.0 | 99.7 | 9.4 |
| 28 | Ade | Ade | TCA | 1.2 | 99.5 | 0 |
| 29 | Ade | Ade | Ade | 3.0 | | 50 |

[a]Compounds were tested at 300 μm.
[b]Inhibition of HIV-1 replication was determined by HIV-1-induced syncytia formation (fold reduction) for each compound. The number of syncytia/$10^4$ cells was 121 ± 16 for the control Sup T1 cells. The mean of triplicate determinations is shown; variance did not exceed 5–10%.
[c]Percent inhibition of reverse-transcriptase (HIV-1 RT) activity. Control values for HIV-1 RT activity ranged from 15000 to 16000 dpm incorporated. The mean of duplicate determinations is shown; variance did not exceed 5–10%.
[d]The activation of recombinant human RNase L was measured as the percent hydrolysis of poly(U)-3'-[$^{32}$P]pCp in the presence of the trimers 22–29. The mean of duplicate determinations is shown; variance did not exceed 5–10%.

The TCA-containing trimers 26–28 inhibited HIV-1 replication to the same extent as naturally occurring trimer 29, as determined by the inhibition of HIV-1-induced syncytia formation. In contrast to the trimers 26–28, the Ade[Bn]-containing trimers 22–25 inhibited HIV-1-induced syncytia formation>1500-fold. On the other hand, the TCA-containing trimers 26–28 inhibited HIV-1 RT activity by 99.7, 99.7, and 99.5%, respectively; however, the inhibition of HIV-1 RT activity by the Ade[Bn]-containing trimers 22–25 was dependent on the position of the Ade[Bn] group in the oligonucleotide chain. The trimer 22, being $N^6$-benzyl-substituted at the 5'-terminus, inhibited HIV-1 RT activity by 33% compared to the trimers 23–25, which inhibited HIV-1 RT activity by 7.6, 16.7, and 10.6%. The TCA- and Ade[Bn]-containing (2'-5')trimers inhibited recombinant human GST-RNase L activity as a function of the change in structure of the base moiety. The (2'-5')trimer 26 with the TCA moiety at the 5'-terminus activated GST-RNase L by 87.7%, compared to 50% hydrolysis of poly(U)-3'-[$^{32}$P]pCp with naturally occurring trimer 29. The (2'-5')trimers 22–25 with the Ade[Bn] moiety instead of adenine activated GST-RNase L by 37.4, 34.8, 0, and 13.6%, respectively. These data indicate that the adenine moiety at the 2',3'-terminus of the (2'-5') oligoadenylate trimer core 29 is essential for the activation of recombinant human RNase L.

Chemical Synthesis of Core Compounds

The synthesis of the unphosphorlyated compounds of the present invention is illustrated by the following non-limiting examples.

General

TLC: Precoated silica gel thin-layer sheets 60 F 254 from Merck. Prep. column chromatography (CC): silica gel (Merck 60, 63–200 μm). Ion-exchange chromatography: DEAE-Servacel 23-SS (Serva). M.p.: Gallenkamp melting-point apparatus; no correction. UV/VIS: Specord UV-VIS (Carl Zeiss, Germany); $\Lambda_{max}$ in mn (log ε). $^1$H-NMR: Bruker WM-360; δ in ppm rel. to SiMe$_4$.

PREPARATION 1

$N^6$-Benzyl-5'-O-(monomethoxytrityl)adenosine (2)

To a solution ("soln.") of $N^6$-benzyladenosine (1, 1.67 g, 4.67 mmol) in pyridine (17 ml), 4-methoxytrityl chloride (2 g, 6.54 mmol) was added at r.t. The mixture was stirred at room temperature ("r.t.") for 20 h and then added dropwise to a mixture of $H_2O$ and ice (800 g). The precipitate was filtered off, dissolved in $CHCl_3$ (150 ml), and washed with $H_2O$ (2×40 ml). The organic layer was dried ($Na_2SO_4$) and evaporated. The residue was purified by CC (silica gel, 15×3.5 cm, $CHCl_3$, then $CHCl_3$/MeOH 20:1) and finally crystallized from EtOH: 2.5 g (85%) of 2. M.p 165–167°. UV (MeOH): 234 (4.21), 271 (4.30). $^1$H-NMR (($D_6$) DMSO): 8.40 (s, NH); 8.27, 8.13 (2s, H—C(2) H—C(8)); 7.37–6.82 (m, 19 arom. H); 5.93 (dd,H—C(1')); 5.55 (d, OH—C(2')); 5.22 (d, OH—C(3')); 4.70(s,PhCH$_2$); 4.36 (dd, H—C(2')); 4.30 (m,H—C(3')); 4.05 (m,H—C(4')); 3.71 (s, MeO); 3.21 (d, 2H—C(5')). Anal. calc. for $C_{37}H_{35}N_3O_3$ (629.7: C 70.57, H 5.60, N 11.12; found: C 70.43, H 5.56, N 11.21.

PREPARATION 2

2',3'-Di-O-benzoyl-$N^6$-benzyl-5'-O-(monomethoxytrityl) adenosine (3), 2'-O-Benzoyl-$N^6$-benzyl-5'-O-(monomethoxytrityl)adenosine (4), and 3'-O-Benzoyl-$N^6$-benzyl-5'-O-(monomethoxytrityl)adenosine (5)

A soln. of benzoyl cyanide (0.27 g, 2.06 mmol) in MeCN (20 ml) was added at r.t. within 30 min to a soln. of 2, Et$_3$N (2.9 ml), and 4-(dimethylamnino)pyridine (DMAP; 50 mg) in MeCN (30 ml). The mixture was stirred at r.t. for 18 h and evaporated. Purification by CC (silica gel, 30×3.5 cm, hexane/AcOET 4:1→1:4) gave, after drying under high vacuum, 0.5 g (38%) of 3, 0.15 g (13%) of 4, and 0.54 g (46%) of 5 as colorless foam.

(3): UV(MeOH): 232 (4.60), 272 (4.36). $^1$H-NMR (($D_6$) DMSO): 8.53 (s, NH): 8.38, 8.17 (2s, H—C(2), H—C(8)); 7.94–6.79(m,29 arom. H); 6.52 (d,H—C(1')); 6.47 (dd,H—C(2')); 6.20 (dd,H—C(3')); 4.72 (s,PhCH$_2$); 4.60 (m, H—C(4')); 3.68 (s, MeO); 3.43 (m, 2H—C(5')). Anal. calc. for $C_{51}H_{43}N_5 7O-(837.9)$: C 73.10, H 5.17, N 8.35; found: C 73.32, H 5.20, N. 8.24.

(4): UV(MeOH): 233 (4.45), 272 (4.32): $^1$H-NMR (($D_6$) DMSO): 8.50 (s, NH); 8.36, 8.20 (2s, H—C(2), H—C(8)); 8.07–6.83 (m, 24 arom. H); 6.37 (d, H—C(1')); 6.09 (dd. H—C(2')); 5.75 (d, OH—C(3')); 4.90 (dd, H—C(3')); 4.72 (s, PhCH$_2$); 4.22 (m, H—C(4')); 3.71 (s, MeO); 3.30 (m, 2H—C(5')). Anal. calc. for $C_{44}H_{39}N_5O_6$ (733.8): C 72.01, H 5.35, N 9.54; found C 72.18, H 5.30, N 9.37.

(5): UV(MeOH): 233 (4.48), 272 (4.34). $^1$H-NMR (($D_6$) DMSO): 8.47 (s, NH): 8.35, 8.14 (2s, H—C(2), H—C(8')); 8.07–6.80 (m. 24 arom. H); 6.04 (d, H—C(1')); 5.98 (d, OH—C(2')); 5.64 (dd, H—C(3')); 5.23 (dd, H—C(2')); 4.72 (s, PhCH$_2$); 4.39 (m, H—C(4')); 3.67 (s, MeO); 3.36 (m, 2H—C(5')). Anal. calc. for $C_{44}H_{39}N_5O_6$ (733.8): C 72.01, H 5.35, N 9.54; found C 72.20, H 5.40, N 9.40.

PREPARATION 3

2',3'-Di-O-Benzoyl-$N^6$-benzyladenosine (6)

A soln. of 3 (0.1 g. 0.12 mmol) was stirred with 2% TsOH in $CH_2Cl_2$/MeOH 7:3 (10 ml) for 10 min. The mixture was diluted with CHCl₃ (100 ml) and washed with H₂O (2×50 ml). The org. phase was dried (Na₂SO₄) and evaporated and the crude product purified by CC (silica gel, 10×2.5 cm, CHCl₃). Amorphous solid. UV(MeOH): 232 (4.32), 272 (4.36), $^1$H-NMR ((D₆) DMSO): 8.65 (s, NH); 8.49, 8.25 (2s, H—C(2), H—C(8)); 8.07–7.11 (m, 15 arom. H); 6.54 (d, H—C(1')); 6.30 (dd, H—C(2')); 5.92 (dd, H—C(3')); 5.86 (t. OH—C(5')); 4.72 (s, PhCH₂); 4.55 (m, H—C(4')); 3.83 (m, 2H—C(5')); Anal. calc. for C₃₁H₂₇N₅O₆ (565.5: C 65.83, H 4.81, N 12.38; found: C 65.91 H 4.85, N 12.29.

PREPARATION 4
1-[5-O-(Monomethoxytrityl)-β-D-ribofuranosyl]-1H-1,2,4-triazole-3-carboxamide (8).

A mixture of ribavirin (7; 1 g, 4.1 mmol) and 4-methoxytrityl chloride (1.5 g, 4.9 mmol) in pyridine (50 ml) was stirred at r.t. for 48 h, evaporated, and co-evaporated with toluene (2×30 ml). The residue was dissolved in CHCl₃ (100 ml) and washed with H₂O (2×50 ml). The org. layer was dried (Na₂SO₄), evaporated to a small volume (ca. 7 ml), and precipitated with hexane to give, after drying under high vacuum, 1.95 g (92%) of 8. UV (MeOH); 231 (4.27). $^1$H-NMR ((D₆) DMSO): 8.83 (s, H—C(5)); 7.75, 7.63 (2s, NH₂); 7.36–6.83 (m, 10 arom. H): 5.94 (d, H—C(1)), 5.65 (d. OH—C(2')); 5.20 (d, OH—C(3')); 4.20 (m, H—C(2')); 4.31 (m, H—C(3')); 4.07 (m. H—C(4')); 3.73 (s, MeO); 3.13 (m, 2H—C(5')). Anal. calc. for C₂₈H₂₈N₄O₆ (516.5): C 65.10, H 5.46, N 10.84; found: C 65.30, H 5.30, N 10.79.

PREPARATION 5
1-[2,3-Di-O-Benzoyl-5-O-(monomethoxytrityl)-β-D-ribofuranosyl]-1H-1,2,4-triazole-3-carboxamide (9) and 1-[3-O-Benzoyl-5-O-monomethoxytrityl)-β-D-ribofuranosyl]-1H-1,2,4-triazole Carboxamide (10)

To a soln. of 8 (1.85 g, 3.48 mmol) in MeCN (40 ml) Et₃N(6.3 ml), and DMAP (32 mg, 0.26 mmol): a soln. of benzoyl cyanide (0.55 g, 4.18 mmol) in MeCN (10 ml) was added dropwise within 3 h. The mixture was stirred at r.t. for 18 h and evaporated. Purification by CC (silica gel, 20×3.5 cm, hexane/AcOEt 3:1→AcOEt) gave, after drying under high vacuum, 0.4 g (16%) of 9 and 1.3 g (57% of 10 as colorless foams.

(9): UV (MeOH): 231 (4.63). $^1$H-NMR ((D₆)DMSO) :8.94 (s, H—C(5)); 7.93–6.78 (m, 26H, NH₂, arom. H); 6.65 (d, H—C(1')); 6.10 (dd, H—C(2')); 6.03 (dd. H—C(3')); 4.60 (m, H—C(4')); 3.69 (s, MeO); 3.43 (m, 2H—C(5')). Anal. calc. for C₄₂H₃₆N₄O₈ (724.85): C 69.60, H 5.00, N 7.73; found: C 69.35, H 4.89, N 17.85.

(10): UV (MeOH): 231 (4.47). $^1$H-NMR ((D₆) DMSO): 8.93 (s, H—C(5)); 8.04–6.81 (m, 21H, NH₂, arom. H); 6:12 (d, OH—C(2')); 6.09 (d, H—C(1')); 5.54 (dd, H—C(3')); 4.90 (dd, H—C(2')); 4.43 (m, H—C(4')); 3.70 (s, MeO); 3.30 (m, 2H—C(5')). Anal. calc. for C₃₅H₃₂N₄O₇(620.7): C 67.73, H 5.19, N 9.02; found: C 67.48, H 5.10, N 8.94.

PREPARATION 6
1-(2,3-Di-O-benzoyl-β-D-ribofuranosyl)-1H-1,2,4,-triazole-3-carboxamide (11)

A soln. of 9 (0.36 g, 0.5 mmol) in 80% AcOH (30 ml) was stirred at 50° for 15 min and evaporated. The residue was co-evaporated with EtOH (2×30 ml) and crystallized from EtOH: 176 mg (78%) of 11. M.p. 172–173°. UV (MeOH) :229 (4.54). $^1$H-NMR (D₆) DMSO): 8.95 (s, H—C(5)); 7.95–7.40 (m, 12H, NH₂, arom. H); 6.57 (d, H—C(1')); 6.05 (dd, H—C(2'); 5.87 (dd, H—C(3')); 4.55 (dd, H—C(4')); 3.75 (m, 2H—C(5')). Anal. calc. for C₂₂H₂₀N₄O₇ (452.4): C 58.40, H 4.45, N 12.38; found: C 58.20, H 4.32, N. 12.27.

PREPARATION 7
3'-O-Benzoyl-N⁶-benzyl-5'-O-(monomethoxytrityl) adenosine 2-[2-(4-Nitrophenyl)ethyl Trimethylammonium Phosphate] (13)

To a soln. of 1H-1,2,4-triazole (92 mg, 1.33 mmol) in pyridine (1.3 ml), 2-chlorophenyl phosphorodichloridate (160 mg, 0.65 mmol) was added. After at r.t. for 10 min, the mixture was cooled with ice, and a soln. of 5 (0.32 g, 0.44 mmol) in pyridine (0.9 ml) was added. After 3 h, 2-(4-nitrophenyl)ethanol (0.54 g, 3.25 mmol) was added and the mixture stirred at r.t for 18 h., diluted with CHCl₃ (100 ml), and washed with 0.05M (Et₃NH)HCO₃ (2×50 ml). The org. phase was dried (Na₂SO₄), evaporated, and co-evaporated with toluene (2×20 ml). The residue was dissolved in a soln. of 4-nitrobenzaldoxim (0.72 g, 4.33 mmol) in dioxane/Et₃N/H₂O 1:1:1 (30 ml). After stirring at 4° for 20 h, the mixture was evaporated and the residue purified by CC (silica gel, 10×2.5 cm, CHCl₃/MeOH/Et₃N 95:4:1) 0.38 g (82%) of 13. Colorless foam. UV (MeOH): 233 (4.47), 272 (4.46). H¹-NMR (D₆) DMSO): 8.49 (s, NH); 8.32, 8.13 (2s, H—C (2), H—C(8)); 8.03–6.79 (m, 28 arom. H); 6.27 (d, H—C (1')); 5.86 (dd, H—C(3'); 5.65 (m, H—C(2')); 4.70 (s, PhCH₂); 4.39 (m, H—C(4')); 3.68 (s, MeO). Anal. calc. for C₅₈H₆₂N₇O₁₁P (1064.1): C 65.46, H 5.87, N 9.12 found: C 65.58, H 5.78, N. 8.97.

PREPARATION 8
1-[3-O-Benzoyl-5-O-(monomethoxytrityl)-β-D-ribofuranosyl]-1H-1,2,4-triazole-3-carboxamide 2'-[2-(4-Nitrophenyl)ethyl Triethylammonium Phosphate] (14)

To a mixture of 1H-1,2,4-triazole (0.16 g, 2.38 mmol) and 2-chlorophenylphosphorodichloridate (0.27 g, 1.19 mmol) in pyridine (2.2 ml), a soln. of 10 (0.5 g, 0.81 mmol) in pyridine was added dropwise for 15 min at +4°. After 3 h stirring at r.t., 2-(4-nitrophenyl)ethanol (0.54 g, 3.23 mmol) was added. The mixture was stirred at r.t. for 18 h, diluted with ChCl₃ (200 ml), and washed with 0.05M (Et₃NH) HCO₃ ( 2×100 ml). The org. phase was dried (Na₂SO₄), evaporated, and co-evaporated with toluene (2×50 ml). The residue was dissolved in a soln. of 4-nitrobenzaldoxime (0.45 g, 2.71 mmol) in dioxane/Et₃N/H₂O 1:1:1 (18 ml). The mixture was stirred at r.t. for 24 h, evaporated, and co-evaporated with toluene (2×20 ml). The residue was purified by CC (silica gel, 10×2.5 cm, CHCl₃, and then CHCl₃/MeOH/Et₃N 95:4:1): 0.37 g (48%) of 14. Colorless foam. UV (MeOH): 230 (4.39), 273(4.07). H¹-NMR (D₆) DMSO): 8.94 (s, H—C(5)); 8.05–6.75 (m, 25H, NH₂, arom. H); 6.30 (d,H—C(1')); 5.78,(dd, H—C(3')); 5.61 (m, H—C (2')); 4.45 (m, H—C(4')); 4.25 (m, OCH₂CH₂Ph); 3.69 (s, MeO); 3.31 (m, 2H—C(5')); 2.81 (m, OCH₂CH₂Ph). Anal. calc. for C₄₉H₅₅N₆O₁₂P (951.0): C 61.88, H 5.82, N 8.83 found: C 61.71, H 5.70, N. 8.69

PREPARATION 9
N⁶,3'-O-Dibenzoyladenylyl-{2'-{O^P-[2-(4-nitrophenyl) ethyl]}→5'}-2', 3'-di-O-benzoyl-N⁶-benzyladenosine (16)

A mixture of 6 (56 mg, 0.1 mmol), 15 (151 mg, 0.14 mmol), 1H-tetrazole (59 mg, 0.84 mmol), and TpsCl (85 mg, 0.28 mmol) in pyridine (1 ml) was stirred at r.t for 16 h, diluted with CHCl₃, (50 m), and washed with 0.05M (Et₃NH)HCO₃ (2×15 ml). The org. phase was dried (Na₂SG₄), evaporated, and co-evaporated with toluene (2×15 ml). The residue was dissolved in 2% TsOH soln. (10 ml), and after 10 min, diluted with CHCl₃ (50 m), and washed with 0.05M (Et₃NH)HCO₃. The org layer was dried (Na₂SO₄) and evaporated. The residue was purified by CC (silica gel, 10×2.5 cm, CHCl₃): 105 mg (85%) of 16. Colorless foam. UV (MeOH): 234 (4.70), 272 (4.66). Anal. calc. for C₆₃H₅₄N₁₁O₁₆P (1252.2): C 60.43, H 4.34, N 12.30 found: C 60.59, H 4.42, N. 12.18.

PREPARATION 10
3'-O-Benzoyl-N⁶benzyladenylyl-{2'-{O^P[2-(4-nitrophenyl) ethyl]}→5'}-2',3'-di-O-benzoyl-N⁶-benzyladenosine (17)

As described for 16, with 6 (40 mg, 0.071 mmol), 13 (105 mg, 0.1 mmol) pyridine (0.7 ml), TpsCl (60 mg, 0.188 mmol), 1H-tetrazole (42 mg, 0.59 mmol), 2% TsOH soln. (5.7 ml), and 0.05M ($Et_3NH)HCO_3$. CC (silica gel, 10×2.5 cm, $CHCl_3$) gave 71 mg (81%) of 17. Colorless foam. UV (MeOH): 234 (4.71), 272 (4.65). Anal. calc. for $C_{63}H_{56}N_{11}O_{15}P$ (1238.2): C 61.11, H 4.55, N 12.44 found: C 61.30, H 4.60, N 12.23.

PREPARATION 11

3'-O-Benzoyl-$N^6$-adenylyl-{2'-{$O^P$-[2-(4-nitrophenyl)ethyl]}→5'}-$N^6$,2'-O,3'-O-tribenzoyladenosine (18)

As described for 16, with 12 (40 mg, 0.069 mmol), 13 (102 mg, 0.096 mmol), pyridine (0.7 ml), TpsCl (60 mg, 0.188 mmol), 1H-tetrazole (42 mg, 0.59 mmol), 2% TsOH soln. (5.5 ml), and 0.05M ($Et_3NH)HCO_3$. CC (silica gel, 10×2.5 cm, $CHCl_3$) gave 75 mg (87%) of 18. Colorless foam. UV (MeOH):234 (4.70), 272 (4.66). Anal. calc. for $C_{63}H_{54}N_{11}O_{16}P$ (1252.2): C 60.43, H 4.34, N 12.30; found: C 60.55, H 4.29, N 12.19.

PREPARATION 12

$N^6$,3'-O-Dibenzoyladenylyl-{2'-{$O^P$-[2-(4-nitrophenyl)ethyl]}→5'}-1-(2,3-di-O-benzoyl-β-D-ribofuranosyl)-1,2,4-triazole-3-carboxamide (19)

As described for 16, with 11 (70 mg, 0.15 mmol), 15 (0.2 g, 0.18 mmol), pyridine (2 ml), TpsCl (0.17 g, 0.56 mmol), 1H-tetrazole (80 mg, 1.14 mmol), 2% TsOH soln. (10 ml), and 0.05M ($Et_3NH)HCO_3$. CC (silica gel, 10×2.5 cm, $CHCl_3$→$CHCl_3$/MeOH 19:1) gave 0.13 g (74%) of 19. Colorless foam. UV (MeOH):233 (4.72), 272 (4.35). Anal. calc. for $C_{54}H_{47}N_{10}O_{17}P$ (1139.0): C 56.94, H 4.15, N 12.29; found: C 57.07, H 4.21, N 12.14.

PREPARATION 13

[1-(3-O-Benzoyl-β-D-ribofuranosyl)-1H-1,2,4-triazole-3-carboxamide]yl-{2'-{$O^P$-[2-(4-nitrophenyl)ethyl]}→5'}-$N^6$,2'-O,3'-O-tribenzoyladenosine (20)

As described for 16, with 12 (58 mg. 0.1 mmol), 14 (144 mg, 0.15 mmol), pyridine (2 ml) TpsCl (91 mg, 0.3 mmol), 1H-tetrazole (63 mg, 0.9 mmol). 2% TsOH soln. (10 ml), and 0.05M ($Et_3NH)HCO_3$. CC silica gel, 9×2.5 cm, $CHCl_3$→$CHCl_3$/MeOH 19:1) gave 86 mg (76%) of 20. Colorless foam. UV (MeOH):233 (4.71), 273 (4.36). Anal. calc. for $C_{54}H_{47}N_{10}O_{17}P$ (1139.0):C 56.94, H 4.15, N 12.19; found: C 57.11, H 4.14, N 12.20.

EXAMPLE 1

Adenylyl-(2'-5')-adenylyl-(2'-5')-$N^6$-benzyladenosine Bis(triethylammonium) Salt (22)

A mixture of 15 (127 mg, 0.12 mmol) and 16 (105 mg, 0.08 mmol) in pyridine (0.8 ml), in the presence of Tps Cl (71 mg, 0.23 mmol) and 1H-tetrazole (49 mg, 0.7 mmol), was stirred at r.t. for 18 h, diluted with $CHCl_3$ (50 ml), and washed with 0.05M ($Et_3NH)HCO_3$ 2×20 ml). The org. layer was dried ($Na_2SO_4$), evaporated, and co-evaporated with toluene (2×10 ml). The residue was treated with 2% TsOH soln. (8 ml), stirred for 10 min, diluted with $ChCl_3$ (50 ml), and washed with 0.05M ($Et_3NH)HCO_3$ (2×15 ml). The org. layer was dried ($Na_2SO_4$) and evaporated. The residue was dissolved in 0.5M DBU in pyridine (16.4 ml) and stirred at r.t. for 18 h. Then the soln. was neutralized with 1M AcOH in pyridine (8.2 ml)and evaporated. The residue was dissolved in sat. $NH_3$/MeOH (40 ml), stirred at r.t. for 18 h, and evaporated, and the residue taken up in $CHCl_3$/$H_2O$ 1:1(100 ml). The org. phase was applied to an ion-exchange DEAE-Servacel-23-SS column (20×1.5 cm, linear gradient of 0.005→0.2M ($Et_3NH)HCO_3$ buffer (pH 7.5). The product fractions were evaporated, and co-evaporated with MeOH (3×30 ml). The residual $Et_3NH^+$ salt was lyophilized ($H_2O$): 54 mg (53%) of 22. UV($H_2O$). 263 (4.52). $^1$H-NMR ($D_2O$, t-BuOH as internal standard):6.91, 6.83, 6.73, 6.71,6.62, 6.51 (6s, H—C(2), H—C(8)); 6.13 (m, 5 arom. H); 4.80, 4.67, 4.60 (3d, 3H—C(1')).

EXAMPLE 2

Adenylyl-(2'-5')-$N^6$-benzyladenylyl-(2'-5')-adenosine Bis(triethylammonium) Salt (23)

As described for 22, with 15 (91 mg. 0.08 mmol), 18 (75 mg, 0.06 mmol), pyridine (0.6 ml), TpsCl (51 mg, 0.17 mmol), 1H-tertrazole (35 mg, 0.45 mmol), 2% TsOH soln. (5 ml), 0.5M DBU in pyridine (13.2 ml) 1M AcOH in pyridine (6.6 ml), and sat. $NH_3$ in MeOH (15 ml). Treatment with $CHCl_3$/$H_2O$ 1:1 (100 ml) gave, after ion exchange (DEAE-Servacel 23-SS), 49 mg (67%) of 23. UV ($H_2O$):263 (4.52), $^1$H-NMR ($D_2O$, t-BuOH as internal standard): 6.86, 6.81 (2H), 6.77, 6.56, 6.39 (5s, H—C(2), H—C(8)); 6.08 (m, 5 arom. H); 4.77, 4.73, 4.57 (3d, 3H—C(1')).

EXAMPLE 3

$N^6$-Benzyladenylyl-(2'-5')-adenylyl-(2'-5')-adenosine Bis(triethylammonium) Salt (24)

As described for 22, with 13 (32 mg, 0.03 mmol), 21 (32 mg, 0.025 mol), pyridine (0.3 ml), TpsCl (18 mg, 0.06 mmol), 1H-tetrazole (17 mg, 0.24 mmol), 2% TsOH soln. (3 ml), ),5M DBU in pyridine (3.2 ml), 1M AcOH in pyridine (1.6 ml), and sat. $NH_3$ in MeOU (8 ml). Treatment with $CHCl_3$/$H_2O$ 1:1 (80 ml) gave, after ion exchange (DEAE-Servacel 23-SS), 16 mg (52%) of 24. UV ($H_2O$): 263 (4.48). $^1$H-NMR ($D_2O$, t-BuOH as internal standard): 6.92, 6.85, 6.73, 6.77 (2H), 6.50, (5s, H—C(2), H—C(8)); 6.07 (m, 5 arom. H); 4.85, 4.67, 4.59 (3d, 3H—C(1')).

EXAMPLE 4

$N^6$-Benzyladenylyl-(2'-5')-$N^6$-benzyladenylyl-(2'-5')-$N^6$-benzyladenosine Bis(triethylammonium) Salt (25)

As described for 22, with 13 (85 mg, 0.08 mmol), 17 (71 mg, 0.06 mmol), pyridine (0.6 ml), TpsCl (48 mg, 0.16 mmol), 1H-tetrazole (34 mg, 0.48 mmol), 2% TSOH soln. (4.5 ml, 0.5M DBU in pyridine (9 ml), 1M AcOH in pyridine (4.5 ml), and sat. $NH_3$ in MeOH (30 ml). Treatment with $CHCl_3$/$H_2O$ 1:1 (100 ml) gave, after ion exchange (DEAE-Servacel 23-SS), 27 mg (76%) of 25. UV ($H_2O$): 270 (4.72). $^1$H-NMR ($D_2O$, t-BuOH as internal standard): 6.88, 6.83, 6.79, 6.73, 6.57, 6.50, (6s, H—C(2), H—C(8)); 6.04 (m, 15 arom. H); 4.82, 4.76, 4.62 (3d, 3H—C(1')).

EXAMPLE 5

Adenylyl-(2'-5')-adenylyl-(2'-5')-1-(β-D-ribofuranosyl)-1H-1,2,4-triazole-3-carboxamide Bis(triethylammonium) Salt (26)

As described for 22, with 15 (110 mg. 0.1 mmol), 19 (95 mg, 0.08 mmol), pyridine (0.9 ml), TpsCl (90 mg. 0.3 mmol), 1H-tertrazole (42 mg, 0.59 mmol), 2% TsOH soln. (5 ml), 0.5M DBU in pyridine (10 ml) 1M AcOH in pyridine (5 ml), and sat. $NH_3$ in MeOH (30 ml). Treatment with $CHCl_3$/$H_2O$ 1:1 (100 ml) gave, after ion exchange (DEAE-Servacel 23-SS), 31 mg (34%) of 26. UV ($H_2O$):260 (4.42) $^1$H-NMR ($D_2O$, t-BuOH as internal standard): 7.13, 6.88, 6.83, 6.73, 6.45, (5s, H—C(2), H—C(5), H—C(8)); 4.85, 4.68, 4.50 (3d, 3H—C(1')).

EXAMPLE 6

Adenylyl-(2'-5')-[1-(β-D-ribofuranosyl)-1H-1,2,4-triazole-3-carboxamide]yl-(2'-5')-adenosine Bis(triethylammonium) Salt (27)

As described for 22, with 15 (86 mg, 0.08 mmol), 20 (57 mg, 0.05 mmol), pyridine (0.7 mnl), TpsCl (73 mg. 0.24 mmol), 1H-tertrazole (50 mg, 0.72 mmol), 2% TsOH soln. (4 ml), 0.5M DBU in pyridine (7 ml) 1M AcOH in pyridine (3.5 mol), and sat. $NH_3$ in MeOH (25 ml). Treatment with $CHCl_3/H_2O$ 1:1 (80 ml) gave, after ion exchange (DEAE-Servacel 23-SS), 13 mg (24%) of 27. UV ($H_2O$):260 (4.42), $^1$H-NMR ($D_2O$, t-BuOH as internal standard): 7.06, 6.98, 6.90, 6.80, 6.71, (5s, H—C(2), H—C(5), H—C(8)); 4.87, 4.77, 4.62 (3d, 3H—C(1')).

EXAMPLE 7

1-(β-D-Ribofuranosyl)-1H-1,2,4-triazole-3-carboxamide]yl-(2'-5')-adenylyl-(2'-5')-adenosine Bis(triethylammonium) Salt (28)

As described for 22, with 14 (76 mg. 0.08 mmol), 21 (63 mg, 0.05 mmol), pyridine (0.8 ml), TpsCl (73 mg, 0.24 mmol), 1H-tertrazole (50 mg, 0.72 mmol), 2% TsOH soln. (5 ml), 0.5M DBU in pyridine (8 ml) 1M AcOH in pyridine (4 ml), and sat. $NH_3$ in MeOH (30 ml). Treatment with $CHCl_3/H_2O$ 1:1 (100 ml) gave, after ion exchange (DEAE-Servacel 23-SS), 26 mg (48%) of 28. UV ($H_2O$):260 (4.43), $^1$H-NMR ($D_2O$, t-BuOH as internal standard): 7.06, 6.88 (2H), 6.75, 6.65 (4s, H—C(2), HC(5), H—C(8)); 4.84, 4.73, 4.59 (3d, 3H—C(1')).

Phosphorylation of Core Compounds

The core compounds of the present invention may be 5'-monophosphorylated according to the procedure of Sambrook el al., *Molecular Cloning—A Laboratory Manual*, 2 ed., Cold Spring Harbor Laboratory Press, pp. 5.68–5.71 (1989) with ATP with T4 polynucleotide kinase. 5'-Monophosphorylation may be determined by reverse-phase HPLC analysis and confirmed by the subsequent hydrolysis of each 5'-monophosphate derivative by 5'-nucleotidase. Yields of phosphorylation range from 15% to 60%. In the case where the $R_2$ groups of all internucleotide bonds (Formula I) of the molecule comprise oxygen, i.e., the linkages comprise phosphodiester bonds, the 5'-monophosphates are readily prepared by reacting the corresponding unphosphorylated core compound with $POCl_3$.

The 5'-diphosphate and 5'-triphosphate of the core compounds of the invention may be prepared by following the procedure of Example 8.

EXAMPLE 8

All reactions are performed in glassware oven-dried at 125° C. for 18–24 hr. Core compound (400 OD units at 260 nm) is dissolved in 500 microliters of dry dimethylformamide ("DMF") and dried in vacuo in a 10 ml conical flask at 35° C. This process is repeated three times. To the dry residue, 50 micromoles of triphenylphosphine, 100 micromoles of imidazole and 50 micromoles of dipyridinyl disulfide are added. The mixture is dissolved in 500 microliters dry DMF plus 50 microliters of dry dimethylsulfoxide. The solution is stirred with a stirring bar for 2 hr at room temperature. After 2 hr the solution is homogeneous (after 30 minutes, the solution begins to change to yellow). The solution is transferred dropwise to 10 ml of a 1% NaI/dry acetone (w/v) solution. The clear colorless precipitate which forms is the sodium salt of the 5'-phosphoroimidazolidate. The precipitate is centrifuged at room temperature, the supernatant is decanted, and the precipitate is washed three times with 10 ml dry acetone. The centrifuging is repeated. The precipitate is dried over $P_2O_5$ in vacuo for 2 hr. The precipitate is dissolved in 200 microliters of freshly prepared 0.5 M tributylammonium pyrophosphate in dry DMF. The solution is maintained at room temperature for 18 hr after which time the DMF is removed in vacuo. The residue is dissolved in 0.25M triethylammonium bicarbonate buffer ("TEAB") (pH 7.5). The 5'-di and 5'-triphosphate products are separated using a DEAE-Sephadex A25 column ($HCO_3$-form; 1×20 cm) with a linear gradient of 0.25 M to 0.75 M TEAB. Fractions (10 ml) are collected. The product is observed by ultraviolet spectroscopy at 254 mn. The fractions containing the 5'-di and 5'-triphosphates are separately pooled and dried in vacuo. The TEAB is removed by repeated addition of water followed by lyophilization. The yield of the 5'-diphosphate is about 5%; the yield of the 5'-triphosphate is about 60%.

All references cited with respect to synthetic, preparative and analytical procedures are incorporated by reference.

The present invention may be embodied in other specific forms without departing from the spirit or essential attributes thereof and, accordingly, reference should be made to the appended claims, rather than to the foregoing specification, as indication the scope of the invention.

REFERENCES

1. C. Horndler, R. J. Suhadolnik, N. F. Muto, E. E. Henderson, M.-X. Guang. W. Pfleiderer, *Helv. Chim. Acta* 1997, 80, in press.
2. A. G. Hovanessian, R. E. Brown, J. M. Kerr, *Nature* 1977, 268, 537.
3. P. F. Torrence, in *Biological Response Modifiers. New Approaches to Disease Intervention*, Academic Press, Orlando 1985, p. 77.
4. A. Kimichi, H. Shure, M. Revel, *Nature* 1979, 282, 727.
5. Y. Devash, A. Gera, D. H. Willis, M. Reichman, W. Pfleiderer, R. Charubala, I. Sela, R. J. Suhadolnik, *J. Biol. Chem.* 1984, 259, 3482.
6. S. N. Mikhailov, W. Pfleiderer, *Tetrahedron Lett.* 1985, 26, 2059.
7. P. Herdewijn, R. Charubala, R. Pauwels, E. De Clercq, W. Pfleiderer, *Nucleosides Nucleotides* 1987, 6, 443.
8. K. Kariko, R. W. Sobol, L. Suhadolnik, S. W. Li, N. L. Reichenbach, R. J. Suhadolnik, W. Pfleiderer, *Biochemistry* 1987, 26, 7127.
9. P. Herdewijn, R. Charubala, W. Pfleiderer, *Helv. Chim. Acta* 1989, 72, 1729.
10. R. Charubala, W. Pfleiderer, R. W. Sobol, S. W. L., R. J. Suhadolnik, *Hel. Chim Acta* 1989, 72, 1354.
11. Y. Kitade, Y. Nakata, K. Hirota, Y. Maki, A. Pabuccuoglu, P. F. Torrence, *Nucleic Acids Res.* 1991, 19, 4103.
12. W. Pfleiderer, F. Himmelsbach, R. Charubala, *Bioorg. Med. Chem. Lett.* 1994, 8. 1047.
13. E. I Kvasyuk, T. I. Kulak, I. A. Mikhailopulo, R. Charubala, W. Pfleiderer, *Helv. Chim, Acta* 1995, 78, 1777.
14. W. E. G. Müller, B. E. Weiler, R. Charubala, W. Pfleiderer, L. Leserman, R. W. Sobol, R. J. Suhadolnik, H. C. Schröder, *Biochemistry,* 1991, 30, 2027.
15. H. C. Schröider, R. J. Suhadolnik, W. Pfleiderer, R. Charubala, W. E. G. Müller, *Int. J. Biochem,* 1992, 24, 55.
16. R. Charubala, W. Pfleiderer, in *Progress in Molecular and Subcellular Biology*, Eds., W. E. G. Müller and H. C. Schröder, Springer Verlag, Heidelberg, 1994, vol. 14, p. 114.
17. M. Wasner, E. E. Henderson. R. J. Suhadolnik, W. Pfleiderer, *Helv. Chim, Acta,* 1994, 77, 1757.

18. M. Wasner, R. J. Suhadolnik, S. E. Horvath, M. E. Adelson, N. Kon, M.-X. Guang, E. E. Henderson, W. Pfleiderer, *Helv. Chim Acta* 1996, 79, 619.
19. E. I. Kvasyuk, T. I. Kulak, N. B. Khripach, I. A. Mikhailopulo, E. Uhlmann, R. Charubala, W. Pfleiderer, *Synthesis* 1987, 535.
20. A. I. Zinchenko, V. N. Barai, V. I. Lyachovez, E. I. Kvasyuk, I. A. Mikhailopulo, *Bioorg. Khim.* (Rus.) 1988, 14, 1401.
21. E. I. Kvasyuk, E. N. Kalinichenko, T. I. Kulak, T. L. Podkopaeva, I. A. Mikhailopulo, I. L. Popov, V. N. Barai, A. I. Zinchenko, *Bioorg. Khim.* (Rus.), 1985, 11, 1239.
22. E. I. Kvasuk, T. I. Kulak, G. V. Zaitseva, I. A. Mikhailopulo, *Bioorg. Khim,* (Rus.) 1984, 10, 506.
23. M. Wasner, R. J. Suhadolnik, S. E. Horvath, M. E. Adelson, N. Kon, M.-X. Guang, E. E. Henderson, W. Pfleiderer, *Helv. Chim Acta* 1996, 79, 609.

What is claimed is:

1. A compound of the formula:

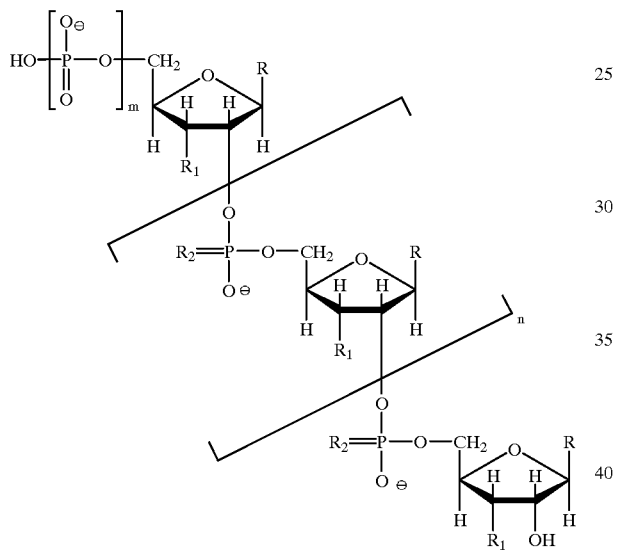

(I)

wherein m is zero, 1, 2 or 3; n is from 1 to 8;

R is independently selected from the group consisting of

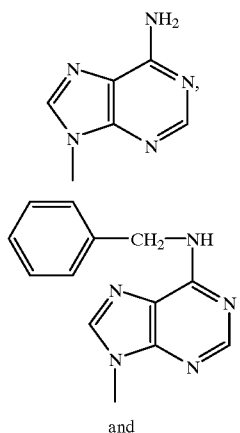

and

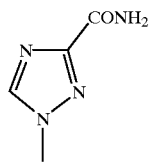

provided that all R may not be

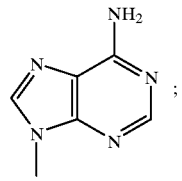

$R_1$ is independently selected from the group consisting of hydroxyl and hydrogen;

$R_2$ is independently selected from the group consisting of oxygen and sulfur;

or water-soluble salt of said compound.

2. A compound according to claim 1 wherein m is 3.
3. A compound according to claim 1 wherein m is 1.
4. A compound according to claim 1 wherein m is 0.
5. A compound according to any of claims 1, 2, 3 or 4 wherein n is 1 or 2.
6. A compound according to claim 5 wherein each $R_1$ is hydroxyl and each $R_2$ is oxygen.
7. A compound according to claim 6 wherein each R is selected from the group consisting of

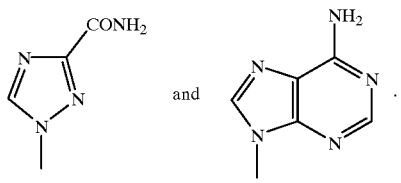

8. A compound according to claim 6 wherein each R is selected from the group consisting of

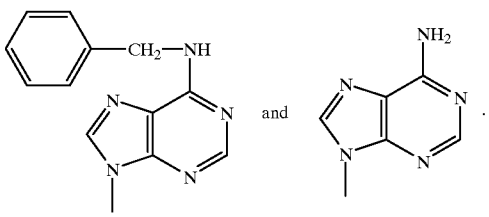

9. A compound according to claim 7 selected from the group consisting of adenylyl-(2'-5') adenylyl-(2'-5')-1-(β-D-ribofuranosyl)-1H-1,2,4-triazole-3-carboxamide, the 5'-mono-, di-, and triphosphates thereof, and water-soluble salts of any of them.

10. A compound according to claim 7 selected from the group consisting of adenylyl-(2'-5')-[1-(β-D-ribofuranosyl)-1H-1,2,4-triazole-3-carboxamide]yl2'-5')-adenosine, the 5'-mono-, di-, and triphosphates thereof, and water-soluble salts of any of them.

11. A compound according to claim 7 selected from the group consisting of 1-(β-D-ribofaranosyl)-1H-1,2,4- triazole-3-carboxamide]-(2'-5')-adenylyl-(2'-5')-adenosine, the 5'-mono-, di-, and triphosphates thereof, and water-soluble salts of any of them.

12. A compound according to claim 8 selected from the group consisting of adenylyl-(2'-5')-adenylyl-(2'-5')-$N^6$-benzyladenosine, the 5'-mono-, di-, and triphosphates thereof, and water-soluble salts of any of them.

13. A compound according to claim 8 selected from the group consisting of adenylyl-(2'-5')-$N^6$-benzyladenylyl-(2'-5')-adenosine, the 5'-mono-, di-, and triphosphates thereof, and water-soluble salts of any of them.

14. A compound according to claim 8 selected from the group consisting of $N^6$-benzyladenylyl-(2'-5')-adenylyl-(2'-5')-adenosine, the 5'-mono, di-, and triphosphates thereof, and water-soluble salts of any of them.

15. A compound according to claim 8 selected from the group consisting of $N^6$-benzyladenylyl-(2'-5')-$N^6$benzyladenylyl-(2'-5')-$N^6$-benzyladenosine, the 5'-mono-, di-, and triphosphates thereof, and water-soluble salts of any of them.

16. A compound or water-soluble salt according to any of claims 9, 10, 11, 12, 13, 14 or 15 wherein m is zero.

17. An antiviral composition comprising a compound or water-soluble salt thereof according to any of claim 1 in combination with an agricultural carrier.

18. An antiviral composition comprising a compound or water-soluble salt thereof according to any of claim 1 in combination with a pharmaceutical carrier.

19. A method of treating viral infection in a plant comprising administering thereto an antiviral effective amount of a compound or water-soluble salt thereof according to any of claim 1.

20. A method of treating viral infection in a mammal comprising administering thereto an antiviral effective amount of a compound or water-soluble salt thereof according to any of claim 1.

* * * * *